(12) United States Patent
Zhou et al.

(10) Patent No.: US 10,149,841 B2
(45) Date of Patent: Dec. 11, 2018

(54) COMPOUND OF 3-HYDROXYL PYRIDINE, PREPARATION METHOD THEREOF AND PHARMACEUTICAL USE THEREOF

(71) Applicant: SHENYANG SUNSHINE PHARMACEUTICAL CO. LTD., Shenyang, Liaoning (CN)

(72) Inventors: Yunlong Zhou, Nanjing (CN); Suixiong Cai, San Diego, CA (US); Guangfeng Wang, Shanghai (CN); Lingling Jiao, Taizhou (CN); Ping Min, Shanghai (CN); Yu Jing, Taizhou (CN); Ming Guo, San Diego, CA (US)

(73) Assignee: SHENYANG SUNSHINE PHARMACEUTICAL CO. LTD., Shenyang (CN)

( * ) Notice: Subject to any disclaimer, the term of this patent is extended or adjusted under 35 U.S.C. 154(b) by 0 days.

(21) Appl. No.: 15/561,435

(22) PCT Filed: Dec. 14, 2015

(86) PCT No.: PCT/CN2015/097246
§ 371 (c)(1),
(2) Date: Sep. 25, 2017

(87) PCT Pub. No.: WO2016/155359
PCT Pub. Date: Oct. 6, 2016

(65) Prior Publication Data
US 2018/0117021 A1  May 3, 2018

(30) Foreign Application Priority Data
Mar. 27, 2015 (CN) .......................... 2015 1 0141553

(51) Int. Cl.
| | | |
|---|---|---|
| *A61K 31/519* | (2006.01) | |
| *A61K 31/4412* | (2006.01) | |
| *A61K 31/44* | (2006.01) | |
| *C07D 213/81* | (2006.01) | |
| *A61P 7/06* | (2006.01) | |
| *A61P 19/02* | (2006.01) | |
| *A61K 45/06* | (2006.01) | |
| *C07D 213/65* | (2006.01) | |

(52) U.S. Cl.
CPC .......... *A61K 31/4412* (2013.01); *A61K 31/44* (2013.01); *A61K 45/06* (2013.01); *A61P 7/06* (2018.01); *A61P 19/02* (2018.01); *C07D 213/65* (2013.01); *C07D 213/81* (2013.01); *Y02P 20/55* (2015.11)

(58) Field of Classification Search
CPC ................ A61K 31/519; A61K 31/517; A61K 31/5365; C07D 487/04; C07D 498/04; C07D 239/70
USPC ....... 514/230.5, 258.1, 262.1, 264.11, 265.1; 544/105, 253, 258, 279, 280
See application file for complete search history.

(56) References Cited

U.S. PATENT DOCUMENTS

| | | |
|---|---|---|
| 7,652,041 B2 | 1/2010 | Adams et al. |
| 2004/0254215 A1 | 12/2004 | Arend et al. |
| 2007/0298104 A1 | 12/2007 | Arend et al. |
| 2007/0299086 A1 | 12/2007 | Kawamoto |
| 2008/0293763 A1 | 11/2008 | Arend et al. |
| 2009/0082357 A1 | 3/2009 | Fitch et al. |
| 2010/0113444 A1 | 5/2010 | Duffy et al. |
| 2010/0305097 A1 | 12/2010 | Warshakoon et al. |
| 2010/0331374 A1 | 12/2010 | Wu et al. |
| 2011/0263644 A1 | 10/2011 | Klaus et al. |
| 2012/0309977 A1 | 12/2012 | Lanthier |

(Continued)

FOREIGN PATENT DOCUMENTS

WO   2010059552 A1   5/2010

OTHER PUBLICATIONS

International Search Report from International Patent Application No. PCT/CN2015/097246, dated Mar. 18, 2016.
Chowdhury et al., "The Human Oxygen Sensing Machinery and its Manipulation," Chemical Society Reviews (2008), 37(7), pp. 1308-1319.
Kadin, Jr. et al., "Oxygen Sensing by Metazoans: The Central Role of the HIF Hydroxylase Pathway," Molecular Cell (2008), 30(4), pp. 393-402.
Schofield et al., "Oxygen Sensing by HIF Hydroxylases," Nature Reviews: Molecular Cell Biology (2004), 5(5), pp. 343-354.

(Continued)

*Primary Examiner* — Jeffrey H Murray
(74) *Attorney, Agent, or Firm* — Greer, Burns & Crain, Ltd.

(57) ABSTRACT

A compound of the following formula (I) or a pharmaceutically acceptable salt thereof, wherein $R_1$ and $R_2$ are independently H; $R_3$ is selected from H, a $C_1$-$C_7$ straight-chain, and a branched or cyclic alkyl; and $R_4$, $R_5$, $R_6$, $R_7$, and $R_8$ are each independently selected from $C_1$-$C_7$ alkyl, halo $C_1$-$C_7$ alkyl and the like. Also provided is a method for preparing the compound, pharmaceutical compositions including the compound or pharmaceutically acceptable salts thereof, and uses of the compound or pharmaceutically acceptable salt thereof in the preparation of a medicine for inhibiting HIF prolyl hydroxylase or a medicine for promoting the generation of endogenous EPO.

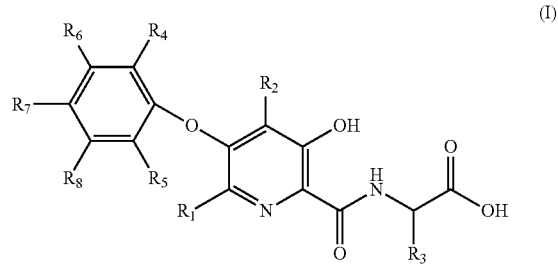

(I)

16 Claims, No Drawings

(56) References Cited

U.S. PATENT DOCUMENTS

2014/0343089 A1 11/2014 Wang et al.
2015/0038528 A1 2/2015 Ho et al.

OTHER PUBLICATIONS

Semenza et al., "A Nuclear Factor Induced by Hypoxia via De Novo Protein Synthesis Binds to the Human Erythropoietin Gene Enhancer at a Site Required for Transcriptional Activation," Molecular and Cellular Biology (1992), 12(12), pp. 5447-5454.
Wang et al., "Purification and Characterization of Hypoxia-inducible Factor 1," The Journal of Biological Chemistry (1995), 270(3), pp. 1230-1237.

COMPOUND OF 3-HYDROXYL PYRIDINE, PREPARATION METHOD THEREOF AND PHARMACEUTICAL USE THEREOF

BACKGROUND

The present invention relates to the field of medicine, and particularly the present invention relates to a 3-hydroxyl compound, a preparation method of the compound and a use thereof for the preparation of a medicament for inhibiting the activity of hypoxiainducible factor (HIF) prolyl hydroxylase.

Hypoxia inducible factor (HIF) is a section of transcriptional activator containing basic helix-loop-helix (bHLH) and PAS (Per/Arnt/Sim) that responds to the hypoxia conditions by mediating a series of gene regulation in biological cells. (Chowdhury, R., Hardy, A, Schofield, C. J., The human oxygen sensing machinery and its manipulation, Chem. Soc. Rev., 2008, 37, 1308-1319; Kaelin, W. G., Jr., Ratcliffe, P. J., Oxygen sensing by metazoans: the central role of the HIF hydroxylase pathway, Mol. Cell, 2008, 30, 393-402; Schofield, C. J., Ratcliffe, P. J., Oxygen sensing by HIF hydroxylases, Nat. Rev. Mol. Cell. Biol., 2004, 5, 343-354).

In 1992, during the study of erythropoientin (EPO, an erythropoiesis-stimulating hormone), Wang et al. found the transcriptional activator that stimulates the generation of EPO in hypoxic cells, and thus named it Hypoxia Inducible Factor, abbreviated as HIF. HIF is essential for cellular adaptation and survival to hypoxia, and the experiments show that under the effect of HIF, cells can still survive even if the oxygen content in the cells is reduced to 1% from normal 20%.

HIF consists of two subunits, HIF-a and HIF-b. HIF-a contains an oxygen-dependent degradation domain (abbreviated as ODDD), which is a key element unit in response to cellular oxygen content. HIF-a can form a stable dimer with HIF-b. After this dimer enters the nucleus, it activates the expression of important enzymes or enzyme systems such as glucose metabolism-related enzymes, GLUT-1, erythropoietin and vascular endothelial growth factor (VEGF), and thus resists the cell hypoxia conditions. HIF-b is a type of aryl hydrocarbon nuclear translator (abbreviated as ARNT), which forms a heterodimer with HIF-a to activate transcription of downstream genes.

To date, three HIF-a subtypes have been discovered, HIF-1a, HIF-2a, and HIF-3a, respectively. HIF-1a, first discovered by Wang in 1995, is widely expressed in human and mouse bodies. HIF-2a was isolated and identified in 1997, which has a protein sequence with 48% similarity to that of HIF-1a and therefore has the similar functions to HIF-1a, however, HIF-2a is only expressed in lung, endothelium and carotid artery. HIF-3a is a newly discovered HIF-a subtype, and little research has been done on it yet.

Studies have shown that the expression of HIF-a in cells is not affected by oxygen content, but HIF-a cannot stably exist in the cells having normal oxygen content, and has a half-life of only 5 minutes. HIF-a can only be stable under hypoxic conditions and thus play the normal function of activation of downstream transcription factors. In the cells having normal oxygen content, the prolyl at positions 402, 564 in the ODDD region of HIF-a was oxidized by prolyl hydroxylase to form 4-hydroxyprolyl, so that HIF-a cannot be dimmed with HIF-b, but soon binds to pVHL protein and then be degraded, and therefore cannot play an anti-hypoxia function. Prolyl hydroxylase (also abbreviated as PHD or EGLN), which plays a key role in the degradation of HIF-a, is a 2-oxoglutatone (2-OG)-dependent oxygenase. With 2-OG and divalent iron ions as prosthetic groups, PHD transfers an oxygen atom to the 4-position of the prolyl molecule to form a hydroxyprolyl, and meanwhile converts 2-OG into one carbon dioxide molecule and succinic acid. Both 2-OG analogs and divalent nickel, cobalt and manganese ions can antagonize the oxidation of prolyl in HIF-a by PHD, and inhibit the degradation of HIF-a, so that HIF-a can successfully be dimmed with HIF-b, and thus stimulates the downstream transcription factors, and ultimately plays an anti-hypoxia function. Studies have found that PHD has three subtypes: PHD1, PHD2, and PHD3. Further studies suggest that inhibition on PHD1 can help to treat skeletal muscle cell degradation, can protect myofibroblasts under ischemic conditions, treat inflammatory enteritis and colitis, and treat heart failure and ischemia in patients with heart disease and kidney disease. However, no study has shown that the other two PHD subtypes have difference in functions.

One of the important roles of HIF is to activate the expression of erythropoietin (EPO) in living organisms. As a glycoprotein hormone, EPO can stimulate red blood cell proliferation, differentiation and maturation. EPO on the one hand can stimulate bone marrow hematopoietic function, timely and effectively increase the number of red blood cells, thereby enhancing the oxygen carrying capacity of the blood. On the other hand, EPO can enhance the body's oxygen binding, transport and supply capacity, and improve hypoxia conditions. Under normal physiological conditions, EPO is mainly synthesized and secreted by the kidney, therefore, a patient with kidney failure will suffer from ischemia because EPO cannot be normally synthesized in the body. In the late 1980s, Amgen company first successfully achieved industrialization of EPO and gradually applied EPO to the patients with anemia caused by chronic kidney failure, AIDS, cancer and chemotherapy. However, with the huge development of EPO generation and application, exogenous EPO administration still faces several problems: 1, EPO is expensive, and is a great burden especially for the patients who need long-term use. 2, as a macromolecule glycoprotein, EPO also has the characteristics of low bioavailability, short half-life in the organism, easy to be hydrolyzed by the enzyme in the gastrointestinal tract, so EPO must be frequently administrated by injection, which limits the probability of patient's self-administration, and brings great inconvenience to the patients. 3, Industrially synthetic EPO still cannot avoid the immunogenicity and the product has certain medication risks.

Due to these problems in the use of exogenous macromolecule EPO, it will be very promising to replace exogenous EPO and bring the patients more choices by developing small molecule HIF prolyl hydroxylase inhibitors to inhibit the HIF-a degradation, thereby stimulating the generation of endogenous EPO in human body.

So far, two HIF prolyl hydroxylases, Akebia's AKB-6548 and Fibrogen's FG-4592, have been introduced into the clinical phase II study. (Refer to WO 2012170377A1, US2010331374A1, US2010305097A1, P&GUS2007299086A1, US2004254215A1, US2007298104A1, US2009082357A1, US2010113444A1, WO2013134660, WO2010059552A1).

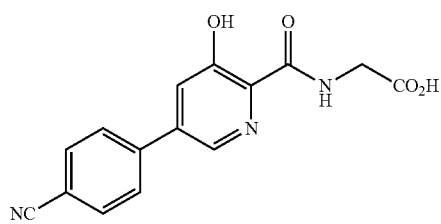

AKB-6548

-continued

FG-4592

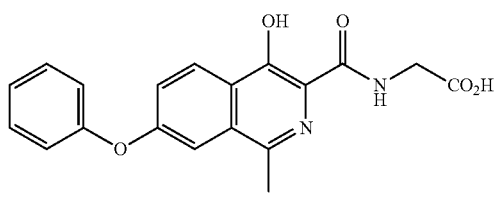

SUMMARY OF THE INVENTION

It is an object of the present invention to provide a novel 3-hydroxypyridine compound or a pharmaceutically acceptable salt thereof.

It is another object of the present invention to provide a method for preparing the above compound.

It is another object of the present invention to provide a pharmaceutical composition comprising the above compound.

It is a further object of the present invention to provide a pharmaceutical use of the above compound or a pharmaceutically acceptable salt thereof.

The objects of the present invention are achieved by the following solutions:

A compound having the following structural formula (I) or a pharmaceutically acceptable salt thereof:

Formula (I)

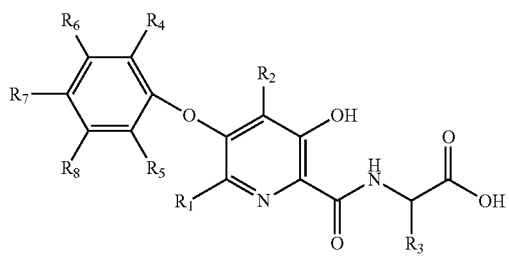

Wherein, $R_1$, $R_2$ are each independently hydrogen.

$R_3$ is selected from the group consisting of hydrogen, a $C_1$-$C_7$ straight-chain, and a branched or cyclic alkyl;

$R_4$, $R_5$, $R_6$, $R_7$, and $R_8$ are each independently selected from $C_1$-$C_7$ alkyl, halo $C_1$-$C_7$ alkyl, $C_{1-3}$ alkoxy, halo $C_{1-3}$ alkoxy, halogen, hydroxy, hydrogen, amino, nitro, cyano and substituted or unsubstituted aromatic ring or an heteroaromatic ring. Or, $R_4$, $R_5$, $R_6$, $R_7$, $R_8$ are bonded to each other with an oxygen bridge to form a compound having the following structural formula (II) or a pharmaceutically acceptable salt thereof:

Formula (II)

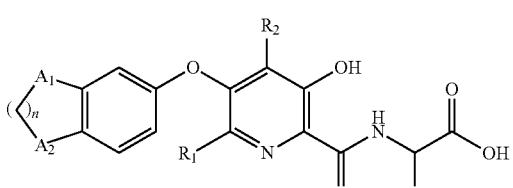

in Formula (II), n is an integer of 1, 2, 3 or 4;

$A_1$ and $A_2$ are each independently an oxygen, carbon or nitrogen atom.

The pharmaceutically acceptable salt of the compound of Formula (I) and (II) is preferably formed by reacting the compound with a pharmaceutically acceptable base. The pharmaceutically acceptable bases include, but are not limited to, sodium hydroxide, sodium carbonate, potassium hydroxide, potassium carbonate, magnesium hydroxide, magnesium oxide, calcium hydroxide, calcium oxide and the like.

The preferred compound of the present invention is selected from the group consisting of the following compounds:

| Compound | Structure |
|---|---|
| 1 | ![structure 1] |
| 2 | ![structure 2] |
| 3 | ![structure 3] |
| 4 | ![structure 4] |
| 5 | ![structure 5] |

| Compound | Structure |
|---|---|
| 6 | 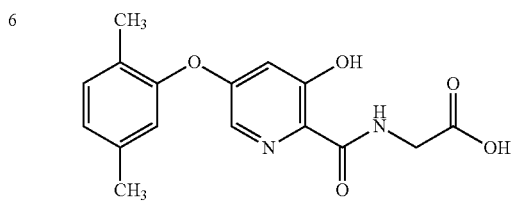 |
| 7 | 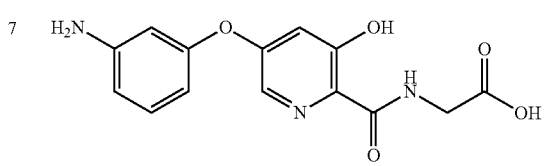 |
| 8 | 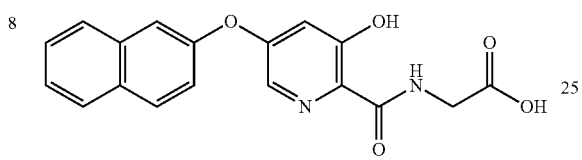 |
| 9 | 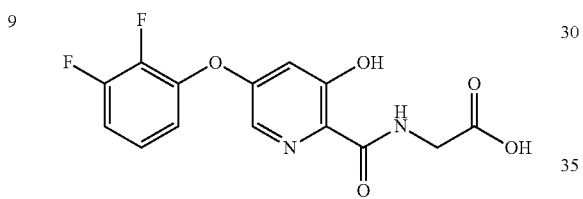 |
| 10 | 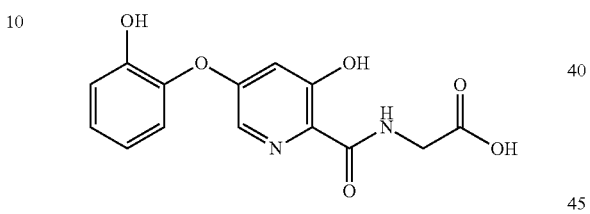 |
| 11 | 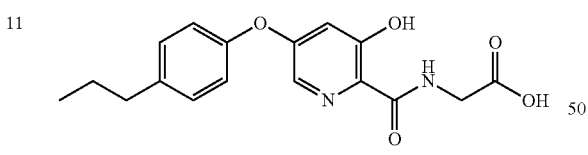 |
| 12 | 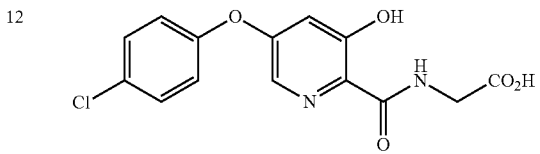 |
| 13 | 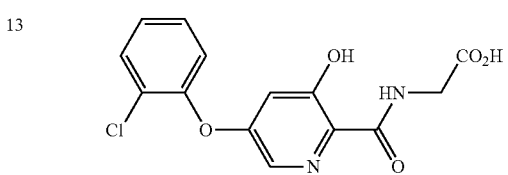 |
| Compound | Structure |
|---|---|
| 14 | 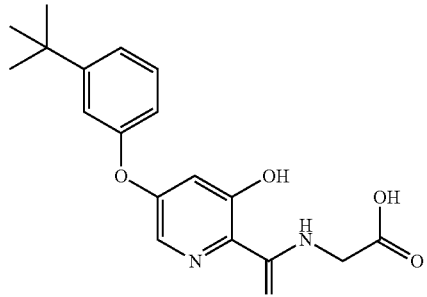 |
| 15 | 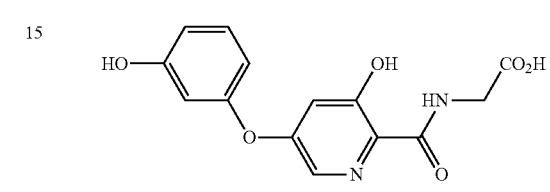 |
| 16 | 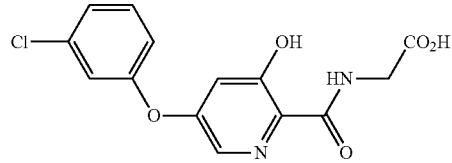 [SMILES: O=C(O)CNC(=O)c1ncc(Oc2cccc(Cl)c2)cc1O] |
| 17 |  |
| 18 | 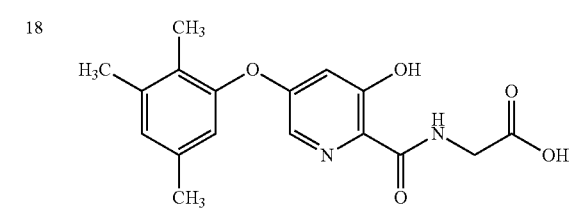 |
| 19 | 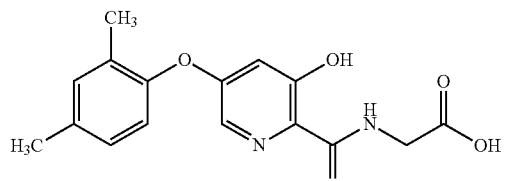 |
| 20 | 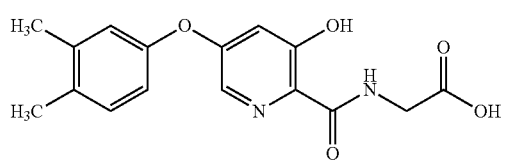 [SMILES: Cc1ccc(Oc2cnc(C(=O)NCC(=O)O)c(O)c2)cc1C] |
| 21 | 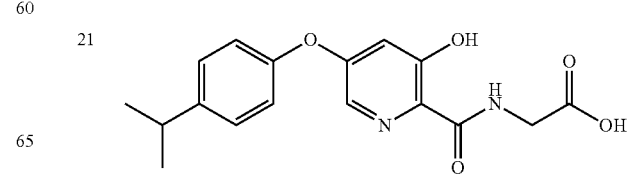 |

-continued

| Compound | Structure |
|---|---|
| 22 | 3-fluorophenoxy-5-(3-hydroxy)pyridine-2-carboxamide-N-CH2-CO2H |
| 23 | 4-fluorophenoxy-5-(3-hydroxy)pyridine-2-carboxamide-N-CH2-CO2H |
| 24 | 4-benzylphenoxy-5-(3-hydroxy)pyridine-2-carboxamide-N-CH2-COOH |
| 25 | 4-methylphenoxy-5-(3-hydroxy)pyridine-2-carboxamide-N-(CH2)4-COOH |
| 26 | 3-trifluoromethylphenoxy-5-(3-hydroxy)pyridine-2-C(O)O-CH2-COOH |
| 27 | 3-chlorophenoxy-5-(3-hydroxy)pyridine-2-carboxamide-N-(CH2)4-COOH |
| 28 | phenoxy-5-(3-hydroxy)pyridine-2-carboxamide-N-C(CH3)2-COOH |
| 29 | phenoxy-5-(3-hydroxy)pyridine-2-carboxamide-N-(CH2)3-COOH |
| 30 | 3-methylphenoxy-5-(3-hydroxy)pyridine-2-carboxamide-N-CH2-COOH |
| 31 | 4-methylphenoxy-5-(3-hydroxy)pyridine-2-carboxamide-N-C(CH3)2-COOH |
| 32 | 4-propylphenoxy-5-(3-hydroxy)pyridine-2-carboxamide-N-CH2-COOH |
| 33 | 2,3-dihydrobenzo[1,4]dioxin-6-yloxy-5-(3-hydroxy)pyridine-2-carboxamide-N-CH2-COOH |
| 34 | 3,4-difluorophenoxy-5-(3-hydroxy)pyridine-2-carboxamide-N-CH2-COOH |
| 35 | phenoxy-5-(3-hydroxy)pyridine-2-carboxamide-N-(CH2)4-COOH |

The synthetic route of the compound of Formula (I) is shown in the following reaction flow:

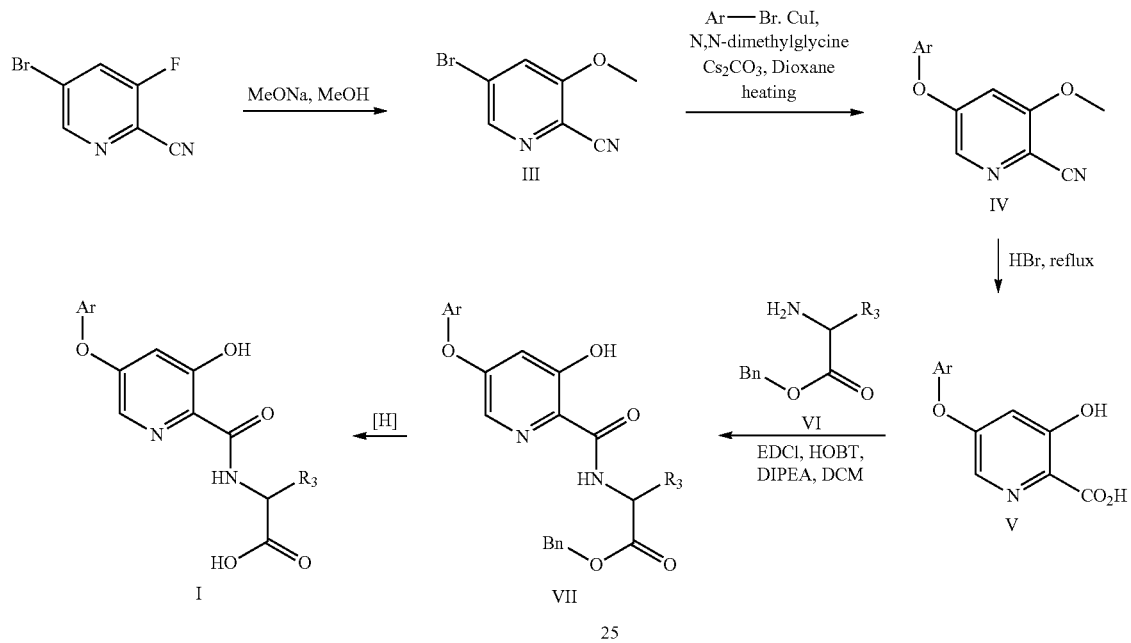

According to one aspect of the present invention, the method for preparing a compound of the present invention comprises the following steps:

step 1: reacting 5-bromo-3-fluoropyridyl-2-carbonitrile

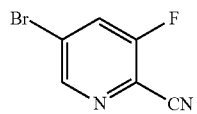

with sodium methoxide in the presence of methanol, to form 5-bromo-3-methoxypyridine-2-carbonitrile (intermediate III)

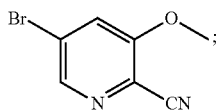

step 2: mixing and heating the intermediate (III) obtained in the step 1 with ArOH and a ligand in a solvent, and subjecting to an Ullman reaction in the participation of a catalyst to form an ether intermediate (IV),

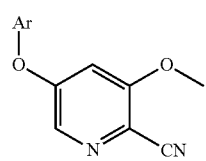

wherein Ar represents

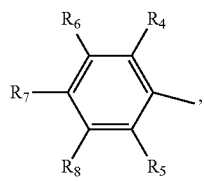

wherein $R_4$, $R_5$, $R_6$, $R_7$ and $R_8$ are each independently selected from $C_1$-$C_7$ alkyl, halo $C_1$-$C_7$ alkyl, $C_1$-$C_3$ alkoxy, halo $C_1$-$C_3$ alkoxy, halogen, hydroxy, hydrogen, amino, nitro, cyano, substituted or unsubstituted aromatic ring or heteroaromatic ring;

step 3: subjecting the intermediate (IV) obtained in the step 2 and HBr to hydrolysis reaction under reflux, to form a 3-hydroxypyridine-2-methanoic acid derivative (V)

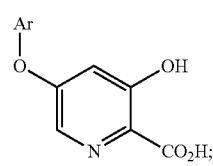

step 4: subjecting the intermediate (V) obtained in the step 3 and α-$R_3$-substituted amino acid benzyl ester (VI) to an amidation reaction in the presence of a condensing agent, to form a benzyl 3-hydroxypyridine-2-carboxylate intermediate (VII);

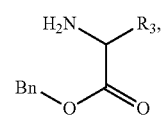

VII step 5: subjecting the intermediate (VII) obtained in the step 4 to hydrogenolysis reaction under hydrogenolysis condition in a solvent in the presence of a catalyst at room temperature to remove the benzyl protecting group, to finally form a compound corresponding to Formula I.

In the above step 1, the starting material 5-bromo-3-fluoropyridine-2-carbonitrile can be obtained by a commercial route, for example, purchased from sigma or J & K. The reaction is carried out at room temperature.

The catalyst in the above step 2 is preferably cuprous$^{(I)}$ iodide. Preferred metal ligands include N, N-dimethylglycine, N-methylproline, N, N-tetramethylethylenediamine and the like. Preferred reaction solvents include 1,4-dioxane, toluene, and tetrahydrofuran. Preferably, the reaction is carried out by heating to 70° C. to 120° C.

In one embodiment, the step 3 comprises subjecting the intermediate (IV) to deprotection and meanwhile hydrolysis reaction in hydrobromic acid/glacial acetic acid to obtain 3-hydroxypyridine-2-methanoic acid intermediate (V). Preferred ratio of hydrobromic acid to glacial acetic acid is 2:1~1:3. Preferred reaction temperature is 90-140° C. Preferred heating reaction time is 6~12 hours.

In the step 4, the α-R$_3$ amino acid benzyl ester (VI) may be in its hydrochloride form. The amino acid α-R$_3$ benzyl ester hydrochloride may be selected from the group consisting of glycine benzyl ester hydrochloride, (α or β) alanine benzyl ester hydrochloride, (α or β) valine benzyl ester hydrochloride, (α or β) leucine benzyl ester hydrochloride, (α or β) isoleucine benzyl ester hydrochloride and the like. Preferred solvents include dichloromethane, chloroform, tetrahydrofuran, 1,4-dioxane, N, N-dimethylformamide, N-methylpyrrolidone and the like. Preferred amidation catalysts include 1-(3-dimethylaminopropyl)-3-ethylcarbodiimide hydrochloride (EDCI), I-hydroxybenzotriazole (HOBT), dicyclohexylcarbodiimide (DCC) and the like. Preferred bases include triethylamine, and N, N-diisopropylethylamine. In one embodiment, the reaction is carried out by mixing and stirring the intermediate (V) with the amino acid benzyl ester hydrochloride (VI) and the condensing agent at room temperature for more than 10 hours.

In the step 5, preferred catalysts include palladium$^{(O)}$/carbon, palladium$^{(II)}$ hydroxide, palladium$^{(II)}$ hydroxide/carbon, platinum$^{(IV)}$ dioxide and the like. The solvent for hydrogenolysis preferably include methanol, ethanol, isopropanol, tetrahydrofuran, ethyl acetate and the like.

The present invention also relates to a use of the compound of the invention or a pharmaceutically acceptable salt thereof in the preparation of a medicament for inhibiting HIF prolyl hydroxylase; a use of the compound of the invention in the preparation of a medicament for promoting the generation of endogenous EPO; a use of the compound of the invention in the preparation of a medicament for stabilizing hypoxia-inducible factor α; a use of the compound of the invention in the preparation of a medicament for treating chronic disease-related anemia in a subject, wherein the chronic disease-related anemia is selected from the group consisting of rheumatoid arthritis, rheumatic fever and inflammatory bowel disease; a use of the compound of the invention in the preparation of a medicament for increasing the production of inflammatory cytokines in a subject, wherein the inflammatory cytokines include tumor necrosis factor, interleukin and interferon; a use of the compound of the invention in the preparation of a medicament for treating anemia in a subject that is resistant to the treatment of exogenous erythropoietin administration, wherein the compound enhances the response of hematopoietic precursor cells to the erythropoietin; a use of the compound of the invention in the preparation of a medicament for increasing the production of a factor required for iron ingestion, iron transport and iron utilization in a subject, wherein the factor is selected from the group consisting of erythrocyte aminolevulinic acid synthase, transferrin, transferrin receptor and plasma ceruloplasmin.

The present invention also relates to a method for inhibiting HIF prolyl hydroxylase in a subject comprising administering to the subject a compound of the invention or a pharmaceutically acceptable salt thereof; to a method for promoting the generation of endogenous EPO in a subject comprising administering to the subject a compound of the invention or a pharmaceutically acceptable salt thereof; to a method for stabilizing hypoxia-inducible factor α in a subject comprising administering to the subject a compound of the invention or a pharmaceutically acceptable salt thereof; to a method for treating chronic disease-related anemia in a subject comprising administering to the subject a compound of the invention or a pharmaceutically acceptable salt thereof, wherein the chronic disease-related anemia is selected from the group consisting of rheumatoid arthritis, rheumatic fever and inflammatory bowel disease.

The present invention also relates to a method for increasing the production of inflammatory cytokines in a subject comprising administering to the subject a compound of the invention or a pharmaceutically acceptable salt thereof, wherein the inflammatory cytokines include tumor necrosis factor, interleukin and interferon.

A further aspect of the present invention relates to a method for treating anemia in a subject that is resistant to the treatment of exogenous erythropoietin administration comprising administering to the subject a compound of the invention or a pharmaceutically acceptable salt thereof, wherein the compound enhances the response of hematopoietic precursor cells to the erythropoietin.

The present invention also relates to a method for increasing the production of a factor required for iron ingestion, iron transport and iron utilization in a subject comprising administering to the subject a compound of the invention or a pharmaceutically acceptable salt thereof, wherein the factor is selected from the group consisting of erythrocyte aminolevulinic acid synthase, transferrin, transferrin receptor and plasma ceruloplasmin.

DETAILED DESCRIPTION

The following examples of the present invention are for illustrative purposes only and are not intended to limit the invention, and suitable variations of the invention may be made without departing from the spirit and the scope of the invention as defined by the appended claims.

Example 1

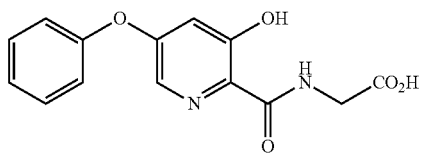 [SMILES: O=C(O)CNC(=O)c1ncc(Oc2ccccc2)cc1O]

2-(3-hydroxy-5-phenoxy-2-pyridylformamido) acetic acid (Compound No. 1)

Step 1: Preparation of 5-bromo-3-methoxypyridine-2-carbonitrile

Sodium methoxide (9.7 g, 0.18 mol) in methanol (50 ml) was added dropwise to a suspension of 5-bromo-3-fluoropyridine-2-carbonitrile (30 g, 0.15 mol) in methanol (150 ml) at room temperature. After completion of the dropwise addition, the mixture was reacted for 2 hours while the reaction solution became clear. A small amount of glacial acetic acid was added to the solution to adjust the pH to between 7 and 8, and ice water (300 ml) was added. The reaction solution was concentrated until a solid precipitated, and allowed to stand and cool for 2 hours so that the solid precipitated more thoroughly. The precipitated solid was filtered off and the filter cake was washed with water, collected and air dried at room temperature to obtain 5-bromo-3-methoxypyridine-2-carbonitrile as a white solid (24 g, 75% yield).

Step 2: Preparation of 3-methoxy-5-phenoxypyridine-2-carbonitrile 5-bromo-3-methoxypyridine-2-carbonitrile (1.33 g, 14.1 mmol), phenol (1 g, 4.7 mmol), cuprous iodide (266 mg, 1.4 mmol), N,N-dimethylglycine (144 mg, 1.4 mmol), cesium carbonate (2.3 g, 7.05 mmol) and 1,4-dioxane (10 ml) were mixed and stirred at 120° C. overnight under the protection of nitrogen. The reaction solution was concentrated and partitioned between ethyl acetate (50 ml) and water (30 ml). The ethyl acetate layer was concentrated and subjected to column chromatography to obtain 3-methoxy-5-phenoxy-pyridin-2-carbonitrile as a solid (769 mg, yield 72%).

Step 3: Preparation of 3-hydroxy-5-phenoxypyridine-2-methanoic acid 3-methoxy-5-phenoxypyridine-2-carbonitrile (600 mg) was dissolved in glacial acetic acid (15 ml), added with hydrobromic acid solution (15 ml) and reacted at 120° C. for 8 hours. The reaction solution was cooled to 25° C. and allowed to stand for 8 hours to precipitate a solid. The solid was filtered and the filter cake was washed with water, collected and dried under reduced pressure to obtain 3-hydroxy-5-phenoxypyridine-2-methanoic acid as a white solid (370 mg, yield 60%).

Step 4: Preparation of benzyl 2-(3-hydroxy-5-phenoxypyridine-2-formamido) acetate 3-hydroxy-5-phenoxypyridine-2-carboxylic acid (89 mg, 0.38 mmol), glycine benzyl ester hydrochloride (116 mg, 0.58 mmol), EDCI (110 mg, 0.58 mmol), HOBT (52 mg, 0.385 mmol) were added to dichloromethane (5 ml) to form a suspension, and diisopropylethylamine (75 mg, 0.578 mmol) was added dropwise to the suspension. After completion of the dropwise addition, the mixture was reacted at room temperature for 8 hours. The reaction solution was diluted with dichloromethane (50 ml) and the dichloromethane solution was washed with water (30 ml). The organic phase was collected and evaporated to remove the organic solvent. The residue was subjected to column chromatography, eluting with ethyl acetate/petroleum ether (1/4) to obtain benzyl 2-(3-hydroxy-5-phenoxypyridine-2-formamido) acetate (106 mg, yield 73%).

Step 5: Preparation of 2-(3-hydroxy-5-phenoxypyridine-2-formamido) acetic acid

Benzyl 2-(3-hydroxy-5-phenoxypyridine-2-formamido) acetate (106 mg) was dissolved in methanol (10 ml), added with 10% palladium$^{(II)}$ hydroxide carbon (10 mg) under nitrogen atmosphere, and then stirred at room temperature for 10 hours while adding hydrogen gas. The catalyst was removed by filtration and the filtrate was concentrated to obtain 2-(3-hydroxy-5-phenoxypyridine-2-formamido) acetic acid as a solid (46 mg, yield 57%).

1H NMR (400 MHz, DMSO-d6) δ 12.55 (s, 1H), 9.21 (t, J=6.2 Hz, 1H), 8.00 (d, J=2.4 Hz, 1H), 7.54-7.40 (m, 2H), 7.34-7.17 (m, 3H), 6.83 (d, J=2.4 Hz, 1H), 3.97 (d, J=6.2 Hz, 1H).

Example 2

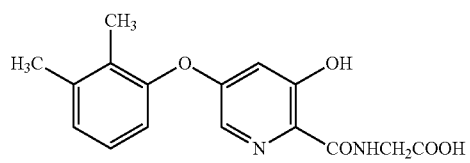

2-(5-(2,3-dimethylphenoxy)-3-hydroxypyridine-2-formamido) acetic acid (Compound No. 5)

Step 1: Preparation of 5-bromo-3-methoxypyridine-2-carbonitrile

Sodium methoxide (9.7 g, 0.18 mol) in methanol (50 ml) was added dropwise to a suspension of 5-bromo-3-fluoro-pyridine-2-carbonitrile (30 g, 0.15 mol) in methanol (150 ml) at room temperature. After completion of the dropwise addition, the mixture was reacted for 2 hours while the reaction solution became clear. A small amount of glacial acetic acid was added to the solution to adjust the pH to between 7 and 8, and ice water (300 ml) was added. The reaction solution was concentrated until a solid precipitated, and allowed to stand and cool for 2 hours so that the solid precipitated more thoroughly. The precipitated solid was filtered off and the filter cake was washed with water, collected and air dried at room temperature to obtain 5-bromo-3-methoxypyridine-2-carbonitrile as a white solid (24 g, 75% yield).

Step 2: Preparation of 5-(2,3-dimethylphenoxy)-3-methoxy-pyridine-2-carbonitrile 426 mg of 5-bromo-3-methoxypyridine-2-carbonitrile (2.0 mmol, 1.0 equiv.), 733 mg of 2,3-dimethylphenol (6.0 mmol, 3.0 equiv.), 114 mg of cuprous iodide (0.6 mmol, 0.3 equiv.), 61.8 mg of N,N-dimethylglycine (0.6 mmol, 0.3 equiv.), 1.3 g of cesium carbonate (4.0 mmol, 2.0 equiv.) and 6 ml of 1,4-dioxane were mixed and stirred at 120° C. overnight under the protection of nitrogen. The reaction solution was concentrated and partitioned between ethyl acetate (50 ml) and water (30 ml). The ethyl acetate layer was concentrated and subjected to column chromatography to obtain 410 mg of 5-(2,3-dimethylphenoxy)-3-methoxy-pyridine-2-carbonitrile as a pale yellow solid, 80.7%.

Step 3: Preparation of 5-(2,3-dimethylphenoxy)-3-hydroxy-pyridine-2-carboxylic acid 410 mg of 5-(2,3-dimethylphenoxy)-3-methoxy-pyridine-2-carbonitrile (1.61 mmol) was dissolved in 2 ml of glacial acetic acid, added with 6 ml of hydrobromic acid solution and reacted at 120° C. for 8 hours. The reaction solution was cooled to 25° C. and allowed to stand for 8 hours to precipitate a solid. The solid was filtered and the filter cake was washed with water, collected and dried under reduced pressure to obtain 350 mg of 5-(2,3-dimethylphenoxy)-3-hydroxy-pyridine-2-carboxylic acid as a reddish brown solid, 83.9%.

Step 4: Preparation of benzyl {[5-(2,3-dimethylphenoxy)-3-hydroxy-pyridine-2-carbonyl]-amino}-acetate 250 mg of 5-(2,3-dimethylphenoxy)-3-hydroxy-pyridine-2-carboxylic acid (0.96 mmol, 1.0 equiv.), 291.0 mg of glycine benzyl ester hydrochloride (1.45 mmol, 1.5 equiv.), 277.0 mg of 1-(3-dimethylaminopropyl)-3-ethylcarbodiimide hydrochloride (1.45 mmol, 1.5 equiv.), 195.8 mg of 1-hydroxybenzotriazole (1.45 mmol, 1.5 equiv.) were added to 10 ml of dichloromethane to form a suspension, and 187.0 mg of diisopropylethylamine (1.45 mmol, 1.5 equiv.) was added dropwise to the suspension. After completion of the dropwise addition, the mixture was reacted at room temperature for 8 hours. The reaction solution was diluted with dichloromethane (50 ml) and the dichloromethane solution was washed with water (30 ml). The organic phase was collected and evaporated to remove the organic solvent. The residue was subjected to column chromatography, eluting with ethyl acetate/petroleum ether (1/4) to obtain 100 mg of benzyl {[5-(2,3-dimethylphenoxy)-3-hydroxy-pyridine-2-carbonyl]-amino}-acetate as an oil, 25.6%.

Step 5: Preparation of 2-(5-(2,3-dimethylphenoxy)-3-hydroxypyridine-2-formamido) acetic acid 100 mg of benzyl {[5-(2,3-dimethylphenoxy)-3-hydroxy-pyridine-2-carbonyl]-amino}-acetate (0.25 mmol) was dissolved in 10 ml of methanol, added with 20 mg of 10% palladium$^{(II)}$ hydroxide/carbon under nitrogen atmosphere, and then stirred at room temperature for 10 hours while adding hydrogen gas. The catalyst was removed by filtration and the filtrate was concentrated to obtain 39 mg of 2-(5-(2,3-dimethylphenoxy)-3-hydroxypyridine-2-formamido) acetic acid, 49.4%, white solid.

1H NMR (400 MHz, DMSO-d6) δ 12.53 (s, 1H), 9.17 (t, J=6.2 Hz, 1H), 7.97 (d, J=2.4 Hz, 1H), 7.25-7.07 (m, 2H), 7.01-6.94 (m, 1H), 6.55 (d, J=2.4 Hz, 1H), 3.97 (d, J=6.0 Hz, 1H), 2.31 (s, 3H), 2.07 (s, 3H).

Example 3

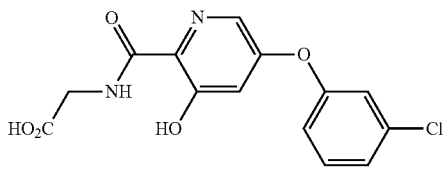 [SMILES: O=C(O)CNC(=O)c1ncc(Oc2cccc(Cl)c2)cc1O]

2-(5-(3-chlorophenoxy)-3-hydroxypyridine-2-formamido) acetic acid (Compound No. 22)

Step 1: Preparation of 5-bromo-3-methoxypyridine-2-carbonitrile

Sodium methoxide (9.7 g, 0.18 mol) in methanol (50 ml) was added dropwise to a suspension of 5-bromo-3-fluoropyridine-2-carbonitrile (30 g, 0.15 mol) in methanol (150 ml) at room temperature. After completion of the dropwise addition, the mixture was reacted for 2 hours while the reaction solution became clear. A small amount of glacial acetic acid was added to the solution to adjust the pH to between 7 and 8, and ice water (300 ml) was added. The reaction solution was concentrated until a solid precipitated, and allowed to stand and cool for 2 hours so that the solid precipitated more thoroughly. The precipitated solid was filtered off and the filter cake was washed with water, collected and air dried at room temperature to obtain 5-bromo-3-methoxypyridine-2-carbonitrile as a white solid (24 g, 75% yield).

Step 2: Preparation of 5-(3-chlorophenoxy)-3-methoxy-pyridine-2-carbonitrile 400 mg of 5-bromo-3-methoxypyridine-2-carbonitrile, 500 mg of 3-chlorophenol, 120 mg of cuprous iodide, 80 mg of N,N-dimethylglycine, 1.5 g of cesium carbonate (4.0 mmol, 2.0 equiv.) and 2 ml of 1,4-dioxane were mixed and stirred at 120° C. overnight under the protection of nitrogen. The reaction solution was concentrated and partitioned between ethyl acetate (50 ml) and water (30 ml). The ethyl acetate layer was concentrated and subjected to column chromatography to obtain 390 mg of 5-(3-chlorophenoxy)-3-methoxy-pyridine-2-carbonitrile as a pale yellow solid.

Step 3: Preparation of 5-(3-chlorophenoxy)-3-hydroxy-pyridine-2-carboxylic acid 390 mg of 5-(3-chlorophenoxy)-3-methoxy-pyridine-2-carbonitrile (0.61 mmol) was dissolved in 1 ml of glacial acetic acid, added with 3 ml of hydrobromic acid solution and reacted at 120° C. for 8 hours. The reaction solution was cooled to 25° C. and allowed to stand for 8 hours to precipitate a solid. The solid was filtered and the filter cake was washed with water, collected and dried under reduced pressure to obtain 300 mg of 5-(3-chlorophenoxy)-3-hydroxy-pyridine-2-carboxylic acid as a reddish brown solid.

Step 4: Preparation of benzyl {[5-(3-chlorophenoxy)-3-hydroxy-pyridine-2-carbonyl]-amino}-acetate 300 mg of 5-(3-chlorophenoxy)-3-hydroxy-pyridine-2-carboxylic acid, 560 mg of glycine benzyl ester hydrochloride, 460 mg of 1-(3-dimethylaminopropyl)-3-ethylcarbodiimide hydrochloride, 330 mg of 1-hydroxybenzotriazole were added to 8 ml of dichloromethane to form a suspension, and 340 mg of diisopropylethylamine was added dropwise to the suspension. After completion of the dropwise addition, the mixture was reacted at room temperature for 8 hours. The reaction solution was diluted with dichloromethane (50 ml) and the dichloromethane solution was washed with water (30 ml). The organic phase was collected and evaporated to remove the organic solvent. The residue was subjected to column chromatography, eluting with ethyl acetate/petroleum ether (1/4) to obtain 150 mg of benzyl {[5-(3-chlorophenoxy)-3-hydroxy-pyridine-2-carbonyl]-amino}-acetate as a pale yellow oil.

Step 5: Preparation of 2-(5-(3-chlorophenoxy)-3-hydroxypyridine-2-formamido) acetic acid 150 mg of benzyl {[5-(3-chlorophenoxy)-3-hydroxy-pyridine-2-carbonyl]-amino}-acetate was dissolved in 10 ml of methanol, added with 15 mg of 10% palladium$^{(II)}$ hydroxide/carbon under nitrogen atmosphere, and then stirred at room temperature for 10 hours while adding hydrogen gas. The catalyst was removed by filtration and the filtrate was concentrated to obtain 70 mg of 2-(5-(2,3-difluorophenoxy)-3-hydroxypyridine-2-formamido) acetic acid as a white solid.

1H NMR (400 MHz, DMSO-d6) 12.57 (s, 1H), 9.24 (t, J=6.2 Hz, 1H), 8.03 (d, J=2.4 Hz, 1H), 7.56-7.30 (m, 2H), 7.30-7.14 (m, 1H), 7.12-6.94 (m, 2H), 3.96 (d, J=6.2 Hz, 1H).

Example 4

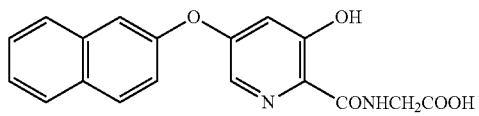

2-(3-hydroxy-5-(naphthalen-2-oxo)pyridine-2-formamido) acetic acid (Compound No. 8)

Step 1: Preparation of 5-bromo-3-methoxypyridine-2-carbonitrile

Sodium methoxide (9.7 g, 0.18 mol) in methanol (50 ml) was added dropwise to a suspension of 5-bromo-3-fluoropyridine-2-carbonitrile (30 g, 0.15 mol) in methanol (150 ml) at room temperature. After completion of the dropwise addition, the mixture was reacted for 2 hours while the reaction solution became clear. A small amount of glacial acetic acid was added to the solution to adjust the pH to between 7 and 8, and ice water (300 ml) was added. The reaction solution was concentrated until a solid precipitated, and allowed to stand and cool for 2 hours so that the solid precipitated more thoroughly. The precipitated solid was filtered off and the filter cake was washed with water, collected and air dried at room temperature to obtain 5-bromo-3-methoxypyridine-2-carbonitrile as a white solid (24 g, 75% yield).

Step 2: Preparation of 3-methoxy-5-(naphthalen-2-oxo)-pyridine-2-carbonitrile 320 mg of 5-bromo-3-methoxypyridine-2-carbonitrile (1.5 mmol, 1.0 equiv.), 649 mg of 2-naphthol (4.5 mmol, 3.0 equiv.), 85.5 mg of cuprous iodide (0.45 mmol, 0.3 equiv.), 46.4 mg of N,N-dimethylglycine (0.45 mmol, 0.3 equiv.), 978 mg of cesium carbonate (3.0 mmol, 2.0 equiv.) and 6 ml of 1,4-dioxane were mixed and stirred at 120° C. overnight under the protection of nitrogen. The reaction solution was concentrated and partitioned between ethyl acetate (50 ml) and water (30 ml). The ethyl acetate layer was concentrated and subjected to column chromatography to obtain 300 mg of 3-methoxy-5-(naphthalen-2-oxo)-pyridine-2-carbonitrile as a red solid, 72.5%.

Step 3: Preparation of 3-hydroxy-5-(naphthalen-2-oxo)-pyridine-2-carboxylic acid 300 mg of 3-methoxy-5-(naphthalen-2-oxo)-pyridine-2-carbonitrile was dissolved in 1.5 ml of glacial acetic acid, added with 4.5 ml of hydrobromic acid solution and reacted at 120° C. for 8 hours. The reaction solution was cooled to 25° C. and allowed to stand for 8 hours to precipitate a solid. The solid was filtered and the filter cake was washed with water, collected and dried under reduced pressure to obtain 200 mg of 3-hydroxy-5-(naphthalen-2-oxo)-pyridine-2-carboxylic acid as a reddish brown solid, 81.8%.

Step 4: Preparation of benzyl {[3-hydroxy-5-(naphthalen-2-oxo)-pyridine-2-carbonyl]-amino}-acetate 250 mg of 3-hydroxy-5-(naphthalen-2-oxo)-pyridine-2-carboxylic acid (0.89 mmol, 1.0 equiv.), 268.2 mg of glycine benzyl ester hydrochloride (1.33 mmol, 1.5 equiv.), 254.0 mg of 1-(3-dimethylaminopropyl)-3-ethylcarbodiimide hydrochloride (1.33 mmol, 1.5 equiv.), 179.6 mg of 1-hydroxybenzotriazole (1.33 mmol, 1.5 equiv.) were added to 10 ml of dichloromethane to form a suspension, and 171.6 mg of diisopropylethylamine (1.33 mmol, 1.5 equiv.) was added dropwise to the suspension. After completion of the dropwise addition, the mixture was reacted at room temperature for 8 hours. The reaction solution was diluted with dichloromethane (50 ml) and the dichloromethane solution was washed with water (30 ml). The organic phase was collected and evaporated to remove the organic solvent. The residue was subjected to column chromatography, eluting with ethyl acetate/petroleum ether (1/4) to obtain 100 mg of benzyl {[3-hydroxy-5-(naphthalen-2-oxo)-pyridine-2-carbonyl]-amino}-acetate as a pale yellow oil, 25.4%.

Step 5: Preparation of 2-(3-hydroxy-5-(naphthalen-2-oxo) pyridine-2-formamido) acetic acid 100 mg of benzyl {[3-hydroxy-5-(naphthalen-2-oxo)-pyridine-2-carbonyl]-amino}-acetate (0.23 mmol) was dissolved in 10 ml of methanol, added with 20 mg of 10% palladium$^{(II)}$ hydroxide/carbon under nitrogen atmosphere, and then stirred at room temperature for 10 hours while adding hydrogen gas. The catalyst was removed by filtration and the filtrate was concentrated to obtain 43 mg of 2-(3-hydroxy-5-(naphthalen-2-oxo) pyridine-2-formamido) acetic acid, 56.2%, white solid.

1H NMR (400 MHz, DMSO-d6) δ 12.57 (s, 1H), 9.25 (t, J=6.4 Hz, 1H), 8.08 (d, J=2.4 Hz, 1H), 7.98 (d, J=8.0 Hz, 1H), 7.92 (d, J=8.0 Hz, 1H), 7.70-7.68 (m, 1H), 7.60-7.47 (m, 2H), 7.46-7.37 (m, 1H), 7.10 (s, 1H), 6.98 (d, J=2.4 Hz, 1H), 4.00 (d, J=6.4 Hz, 1H).

Example 5

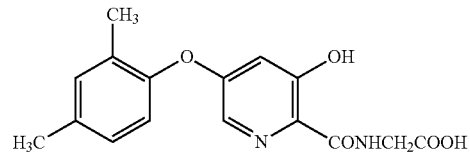

2-(5-(2,4-dimethylphenoxy)-3-hydroxypyridine-2-formamido) acetic acid (Compound No. 19)

Step 1: Preparation of 5-bromo-3-methoxypyridine-2-carbonitrile

Sodium methoxide (9.7 g, 0.18 mol) in methanol (50 ml) was added dropwise to a suspension of 5-bromo-3-fluoropyridine-2-carbonitrile (30 g, 0.15 mol) in methanol (150 ml) at room temperature. After completion of the dropwise addition, the mixture was reacted for 2 hours while the reaction solution became clear. A small amount of glacial acetic acid was added to the solution to adjust the pH to between 7 and 8, and ice water (300 ml) was added. The reaction solution was concentrated until a solid precipitated, and allowed to stand and cool for 2 hours so that the solid precipitated more thoroughly. The precipitated solid was filtered off and the filter cake was washed with water, collected and air dried at room temperature to obtain 5-bromo-3-methoxypyridine-2-carbonitrile as a white solid (24 g, 75% yield).

Step 2: Preparation of 5-(2,4-dimethylphenoxy)-3-methoxy-pyridine-2-carbonitrile 426 mg of 5-bromo-3-methoxypyridine-2-carbonitrile (2.0 mmol, 1.0 equiv.), 733 mg of 2,4-dimethylphenol (6.0 mmol, 3.0 equiv.), 114 mg of cuprous iodide (0.6 mmol, 0.3 equiv.), 61.8 mg of N,N-dimethylglycine (0.6 mmol, 0.3 equiv.), 1.3 g of cesium carbonate (4.0 mmol, 2.0 equiv.) and 6 ml of 1,4-dioxane were mixed and stirred at 120° C. overnight under the protection of nitrogen. The reaction solution was concentrated and partitioned between ethyl acetate (50 ml) and water (30 ml). The ethyl acetate layer was concentrated and subjected to column chromatography to obtain 250 mg of 5-(2,4-dimethylphenoxy)-3-methoxy-pyridine-2-carbonitrile as a pale yellow solid, 49.2%.

Step 3: Preparation of 5-(2,4-dimethylphenoxy)-3-hydroxy-pyridine-2-carboxylic acid 250 mg of 5-(2,4-dimethylphenoxy)-3-methoxy-pyridine-2-carbonitrile (0.98 mmol) was dissolved in 1.5 ml of glacial acetic acid, added with 4.5 ml of hydrobromic acid solution and reacted at 120° C. for 8 hours. The reaction solution was cooled to 25° C. and allowed to stand for 8 hours to precipitate a solid. The solid was filtered and the filter cake was washed with water, collected and dried under reduced pressure to obtain 185 mg of 5-(2,4-dimethylphenoxy)-3-hydroxy-pyridine-2-carboxylic acid as a reddish brown solid, 73.1%.

Step 4: Preparation of benzyl {[5-(2,4-dimethylphenoxy)-3-hydroxy-pyridine-2-carbonyl]-amino}-acetate 185 mg of 5-(2,4-dimethylphenoxy)-3-hydroxy-pyridine-2-carboxylic acid (0.71 mmol, 1.0 equiv.), 215.4 mg of glycine benzyl ester hydrochloride (1.07 mmol, 1.5 equiv.), 204.4 mg of 1-(3-dimethylaminopropyl)-3-ethylcarbodiimide hydrochloride (1.07 mmol, 1.5 equiv.), 144.4 mg of 1-hydroxybenzotriazole (1.07 mmol, 1.5 equiv.) were added to 10 ml of dichloromethane to form a suspension, and 138 mg of diisopropylethylamine (1.07 mmol, 1.5 equiv.) was added dropwise to the suspension. After completion of the dropwise addition, the mixture was reacted at room temperature for 8 hours. The reaction solution was diluted with dichloromethane (50 ml) and the dichloromethane solution was washed with water (30 ml). The organic phase was collected and evaporated to remove the organic solvent. The residue was subjected to column chromatography, eluting with ethyl acetate/petroleum ether (1/4) to obtain 50 mg of benzyl {[5-(2,4-dimethylphenoxy)-3-hydroxy-pyridine-2-carbonyl]-amino}-acetate as a pale yellow oil, 17.3%.

Step 5: Preparation of 2-(5-(2,4-dimethylphenoxy)-3-hydroxypyridine-2-formamido) acetic acid 50 mg of benzyl {[5-(2,4-dimethylphenoxy)-3-hydroxy-pyridine-2-carbonyl]-amino}-acetate (0.12 mmol) was dissolved in 10 ml of methanol, added with 10 mg of 10% palladium$^{(II)}$ hydroxide/carbon under nitrogen atmosphere, and then stirred at room temperature for 10 hours while adding hydrogen gas. The catalyst was removed by filtration and the filtrate was concentrated to obtain 20 mg of 2-(5-(2,4-dimethylphenoxy)-3-hydroxypyridine-2-formamido) acetic acid as a white solid, 51.4%.

1H NMR (400 MHz, DMSO-d6) δ 12.52 (s, 1H), 9.17 (t, J=6.4 Hz, 1H), 7.95 (d, J=2.4 Hz, 1H), 7.23-7.18 (m, 1H), 7.15-7.07 (m, 1H), 7.06-6.94 (m, 1H), 6.56 (d, J=2.4 Hz, 1H), 3.98 (d, J=6.4 Hz, 2H), 2.31 (s, 3H), 2.11 (s, 3H).

Example 6

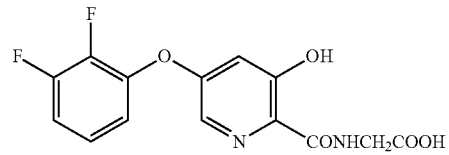

2-(5-(2,3-difluorophenoxy)-3-hydroxypyridine-2-formamido) acetic acid (Compound No. 9)

Step 1: Preparation of 5-bromo-3-methoxypyridine-2-carbonitrile

Sodium methoxide (9.7 g, 0.18 mol) in methanol (50 ml) was added dropwise to a suspension of 5-bromo-3-fluoro-pyridine-2-carbonitrile (30 g, 0.15 mol) in methanol (150 ml) at room temperature. After completion of the dropwise addition, the mixture was reacted for 2 hours while the reaction solution became clear. A small amount of glacial acetic acid was added to the solution to adjust the pH to between 7 and 8, and ice water (300 ml) was added. The reaction solution was concentrated until a solid precipitated, and allowed to stand and cool for 2 hours so that the solid precipitated more thoroughly. The precipitated solid was filtered off and the filter cake was washed with water, collected and air dried at room temperature to obtain 5-bromo-3-methoxypyridine-2-carbonitrile as a white solid (24 g, 75% yield).

Step 2: Preparation of 5-(2,3-difluoro-phenoxy)-3-methoxy-pyridine-2-carbonitrile 426 mg of 5-bromo-3-methoxypyridine-2-carbonitrile (2.0 mmol, 1.0 equiv.), 786 mg of 2,3-difluorophenol (6.0 mmol, 3.0 equiv.), 114 mg of cuprous iodide (0.6 mmol, 0.3 equiv.), 61.8 mg of N,N-dimethylglycine (0.6 mmol, 0.3 equiv.), 1.3 g of cesium carbonate (4.0 mmol, 2.0 equiv.) and 6 ml of 1,4-dioxane were mixed and stirred at 120° C. overnight under the protection of nitrogen. The reaction solution was concentrated and partitioned between ethyl acetate (50 ml) and water (30 ml). The ethyl acetate layer was concentrated and subjected to column chromatography to obtain 160 mg of 5-(2,3-difluoro-phenoxy)-3-methoxy-pyridine-2-carbonitrile as a pale yellow solid, 30.5%.

Step 3: Preparation of 5-(2,3-difluoro-phenoxy)-3-hydroxy-pyridine-2-carboxylic acid 160 mg of 5-(2,3-difluoro-phenoxy)-3-methoxy-pyridine-2-carbonitrile (0.61 mmol) was dissolved in 1 ml of glacial acetic acid, added with 3 ml of hydrobromic acid solution and reacted at 120° C. for 8 hours. The reaction solution was cooled to 25° C. and allowed to stand for 8 hours to precipitate a solid. The solid was filtered and the filter cake was washed with water, collected and dried under reduced pressure to obtain 150 mg of 5-(2,3-difluoro-phenoxy)-3-hydroxy-pyridine-2-carboxylic acid as a reddish brown solid, 92.00%.

Step 4: Preparation of benzyl {[5-(2,3-difluoro-phenoxy)-3-hydroxy-pyridine-2-carbonyl]-amino}-acetate 150 mg of 5-(2,3-difluoro-phenoxy)-3-hydroxy-pyridine-2-carboxylic acid (0.56 mmol, 1.0 equiv.), 169.4 mg of glycine benzyl ester hydrochloride (0.84 mmol, 1.5 equiv.), 160.4 mg of 1-(3-dimethylaminopropyl)-3-ethylcarbodiimide hydrochloride (0.84 mmol, 1.5 equiv.), 113.4 mg of 1-hydroxybenzotriazole (0.84 mmol, 1.5 equiv.) were added to 8 ml of dichloromethane to form a suspension, and 108.4 mg of diisopropylethylamine (0.84 mmol, 1.5 equiv.) was added dropwise to the suspension. After completion of the dropwise addition, the mixture was reacted at room temperature for 8 hours. The reaction solution was diluted with dichloromethane (50 ml) and the dichloromethane solution was washed with water (30 ml). The organic phase was collected and evaporated to remove the organic solvent. The residue was subjected to column chromatography, eluting with ethyl acetate/petroleum ether (1/4) to obtain 70 mg of benzyl {[5-(2,3-difluoro-phenoxy)-3-hydroxy-pyridine-2-carbonyl]-amino}-acetate as a pale yellow oil, 20.1%.

Step 5: Preparation of 2-(5-(2,3-difluorophenoxy)-3-hydroxypyridine-2-formamido) acetic acid 70 mg of benzyl {[5-(2,3-difluoro-phenoxy)-3-hydroxy-pyridine-2-carbonyl]-amino}-acetate (0.17 mmol) was dissolved in 10 ml of methanol, added with 15 mg of 10% palladium$^{(II)}$ hydroxide/carbon under nitrogen atmosphere, and then stirred at room temperature for 10 hours while adding hydrogen gas. The catalyst was removed by filtration and the filtrate was concentrated to obtain 30 mg of 2-(5-(2,3-difluorophenoxy)-3-hydroxypyridine-2-formamido) acetic acid as a white solid, 54.50%.

1H NMR (400 MHz, DMSO-d6) δ 12.82 (s, 1H), 12.59 (s, 1H), 9.25 (t, J=6.4 Hz, 1H), 8.10 (d, J=2.4 Hz, 1H), 7.46-7.35 (m, 1H), 7.34-7.25 (m, 1H), 7.24-7.18 (m, 1H), 7.03 (d, J=2.4 Hz, 1H), 3.99 (d, J=6.4 Hz, 2H).

Biological Example 1: Development and Screening of In Vitro Detection Methods: Promotion of Erythropoietin Expression in Hepatoma Cells Hep3B In Vitro by HIF-PHD2 Inhibitor Compounds The complete medium for culture of experimental hepatoma cells Hep3B (China Center for Type Culture Collection, CCTCC) was MEM (Cat# GNM 41500, GIBCO, provided by Hangzhou Genom Biopharmaceutical Technology Co., Ltd) supplemented with 10% serum FBS (Cat#10099-141, GIBCO) and 1% double-resistant P/S (Cat#GNM 15140, provided by Hangzhou Genom Biopharmaceutical Technology Co., Ltd). Cells were cultured in a 37° C., 5% $CO_2$ incubator. Experimental reagents included dimethyl sulfoxide (for molecular biology, >=99.9%, Catalog# D8418) purchased from Sigma. The ELISA kit was purchased from Quantikine IVD ELISA, Human Erythropoietin (R&D, DEP00). The test control AKB-6548 was prepared by the inventors or obtained by commercial purchase. The test substance was stored at −20° C. in the dark.

The test substance and the positive control substance were fully dissolved in sterile water or dimethylsulfoxide under dark conditions and prepared into a stock solution at a concentration of $10^{-1}$ mol/L or $10^{-2}$ mol/L. Each of the stock solutions was stored at −20° C. MEM medium containing 0.5% FBS was used as a diluent to dilute the stock solution of the test substance, to prepare a diluted test substance at a concentration of 100 μmol/L and 10 μmol/L. 200 μl/well (1.5 or 2.0×10$^4$ cells/well) of hepatoma cells Hep3B complete medium suspension was added to a 96-well culture plate and incubated overnight at 37° C. in a 5% $CO_2$ incubator. The solution in the 96-well culture plate was removed and the cells were washed once with the MEM medium containing 0.5% FBS. 200 μl/well of the test substance was added in the dark, at a dose of 100 μmol/L and 10 μmol/L, and each dose set 2 wells, a test well and a spare well. A cell control well was prepared by replacing the test solution with the diluent (without test substance and solvent). A solvent control well was prepared by replacing the test solution with the diluent containing the corresponding concentration of solvent (dimethylsulfoxide) (without test substance). They were cultured in a 5% $CO_2$ incubator at 37° C. for 24 hours. The supernatant was absorbed as a sample and cryopreserved at −20° C. for later use. 100 μl/well of stop solution was added. OD value was detected by microplate reader A450 nm-A600 nm. The expression level of EPO (mIU/mL) promoted by the test substance was obtained according to the standard curve, and then the ratio of EPO expression content of the test substance to the EPO expression content of the positive control AKB6548 was calculated. The test results are shown in the following table:

| Compound | EPO level/AKB6548 EPO level (10 μM) | Compound | EPO level/AKB6548 EPO level (10 μM) |
| --- | --- | --- | --- |
| 1 | 0.5 | 33 | 0.2 |
| 12 | 0.8 | 27 | 0.0 |
| 2 | 0.3 | 34 | 0.5 |
| 13 | 0.5 | 28 | 0.1 |
| 14 | 1.7 | 35 | 0.2 |
| 16 | 1.1 | 29 | 0.2 |
| 6 | 0.6 | 30 | 1.0 |
| 4 | 1.5 | 20 | 1.4 |
| 3 | 0.8 | 31 | 0.1 |
| 5 | 1.3 | 25 | 0.2 |
| 18 | 1.3 | 26 | 0.6 |
| 8 | 1.5 | 32 | 0.8 |
| 17 | 1.2 | | |
| 9 | 1.5 | | |
| 7 | 0.2 | | |
| 10 | 0.6 | | |
| 21 | 1.5 | | |
| 19 | 1.3 | | |

Biological Example 2: Detection of Inhibitory Effect of the Compounds on PHD2 ($IC_{50}$)

The interaction between hypoxia-inducible factor HIF-1α and VBC complex (von Hippel-Lindau protein-Elongin B-Elongin C, VBC) was detected by Fluorescence polarization (FP) method, to measure the enzyme inhibitory activity of the HIF Prolyl hydroxylases 2 (PHD2) inhibitor compounds.

To a NETN (20 mM Tris.HCl, 100 mM NaCl, 1 mM EDTA, 0.5% NP-40, 1 mM PMSF) buffer containing 200 μM ascorbic acid, 20 μM α-ketoglutaric acid, 100 μM $FeCl_2$ was added FAM-HIF (556-575) at a final concentration of 1 μM in the dark. Subsequently, the desired concentration of the test compound or the positive compound was added (the compound was replaced by the buffer in the negative control and the positive control). Finally, PHD2 was added at a final concentration of 0.5 μg/μl (PHD2 was replaced by the buffer in the negative control). They were mixed well and allowed to stand at room temperature for 30 minutes in the dark followed by 95° C. water bath for 1 minute, and then the reaction was terminated. After the temperature drops to room temperature, the sample was prepared well for use. EBC buffer (50 mM Tris.HCl, 120 mM NaCl, 0.5% NP-40) was added to the corresponding wells of a black 96-well test plate. A GST-VBC complex was added to the corresponding test wells at a final concentration of 300 nM (using the wells containing only EBC buffer as blank wells). Subsequently, the corresponding PHD2 prolyl hydroxylation reaction sample was added in the dark as a substrate with a final concentration of 100 nM. After mixing well, the lateral and longitudinal fluorescence intensity values were measured using a full-wavelength multifunctional microplate reader (TECAN infinite M1000) at an excitation wavelength of 407 nm and an emission wavelength of 518 nm.

The fluorescence polarization (mP) was calculated:

$$mP = 1000 \times (\text{lateral value} - G \text{ factor} \times \text{longitudinal value})/(\text{lateral value} + G \text{ factor} \times \text{longitudinal value})$$

wherein, lateral value=lateral fluorescence intensity value of test well−lateral fluorescence intensity value of blank well, longitudinal value=longitudinal fluorescence intensity value of test well−longitudinal fluorescence intensity value of blank well, PHD2 inhibition rate (%) of the test compound was calculated according to the following formula:

$$\text{Inhibition rate (\%)} = 1 - (mP \text{ test well} - mP \text{ negative control well})/(mP \text{ positive control well} - mP \text{ negative control well}).$$

The $IC_{50}$ was calculated using the non-linear regression data analysis method of Graphpad Prism 4.0 software (Golden software, Golden, Colo., USA).

| Compound No. | $IC_{50}$ (μM) |
|---|---|
| 1 | 84 |
| 5 | 237 |
| 8 | 91 |
| 9 | 15 |
| 19 | 63 |
| 22 | 236 |

What is claimed is:

1. A compound having the following Formula (I) or a pharmaceutically acceptable salt thereof:

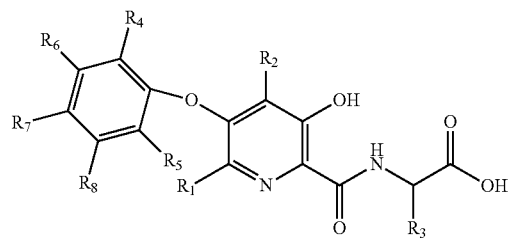

Formula (I)

wherein, $R_1$, $R_2$ are each independently hydrogen;

$R_3$ is selected from the group consisting of hydrogen, a $C_1$-$C_7$ straight-chain, branched or cyclic alkyl;

$R_4$, $R_5$, $R_6$, $R_7$, and $R_8$ are each independently selected from $C_1$-$C_7$ alkyl, halo $C_1$-$C_7$ alkyl, $C_{1-3}$ alkoxy, halo $C_{1-3}$ alkoxy, halogen, hydroxy, hydrogen, amino, nitro, cyano and substituted or unsubstituted aromatic ring or an heteroaromatic ring;

or $R_4$, $R_5$, $R_6$, $R_7$, $R_8$ are bonded to each other with an oxygen bridge to form the following group:

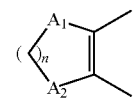

wherein, n is an integer of 1, 2, 3 or 4;

$A_1$ and $A_2$ are each independently an oxygen, carbon or nitrogen atom.

2. A compound having the following Formula (II) or a pharmaceutically acceptable salt thereof:

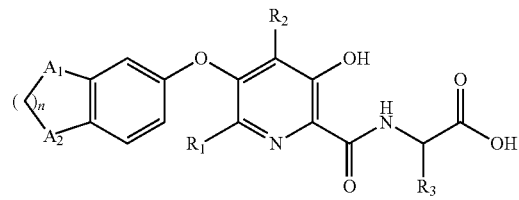

Formula (II)

wherein, n is an integer of 1, 2, 3 or 4;

$A_1$ and $A_2$ are each independently an oxygen, carbon or nitrogen atom.

3. The compound of claim 1 or a pharmaceutically acceptable salt thereof, wherein the pharmaceutically acceptable salt is formed by reacting with a pharmaceutically acceptable base.

4. The compound of claim 1 or a pharmaceutically acceptable salt thereof, wherein the compound is selected from the group consisting of the following compounds:

| Compound | Structure |
|---|---|
| 1 | structure |

| Compound | Structure |
|---|---|
| 2 | 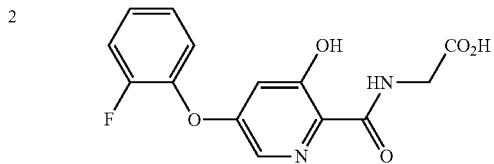 |
| 3 | 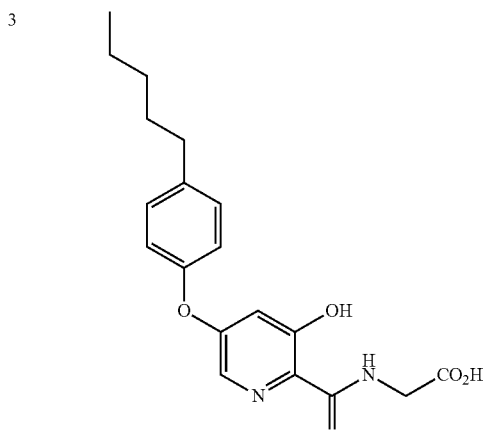 |
| 4 | 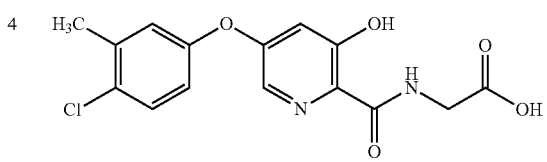 |
| 5 | 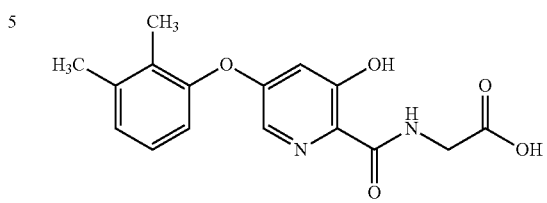 |
| 6 | 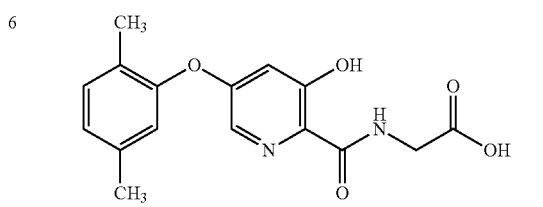 |
| 7 | 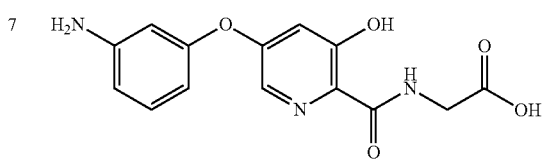 |
| 8 | 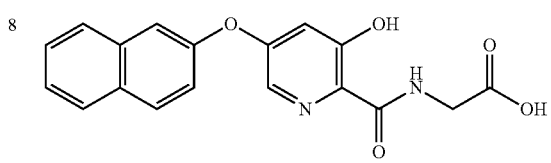 |
| 9 | 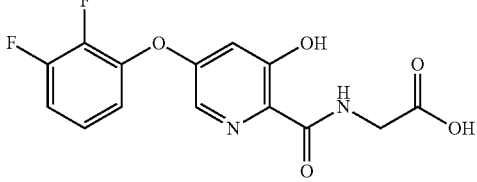 |
| 10 | 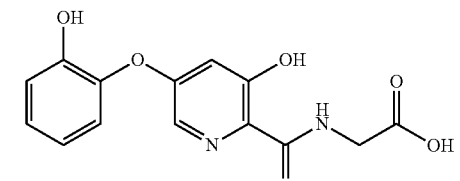 |
| 11 | 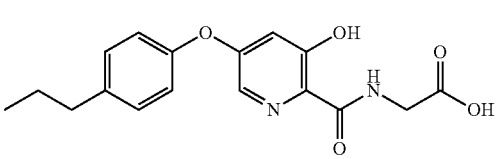 [SMILES: CCCc1ccc(Oc2cnc(C(=O)NCC(=O)O)c(O)c2)cc1] |
| 12 | 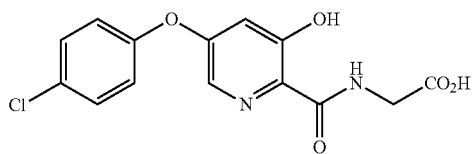 [SMILES: O=C(O)CNC(=O)c1ncc(Oc2ccc(Cl)cc2)cc1O] |
| 13 | 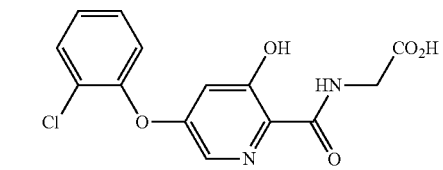 [SMILES: O=C(O)CNC(=O)c1ncc(Oc2ccccc2Cl)cc1O] |
| 14 | 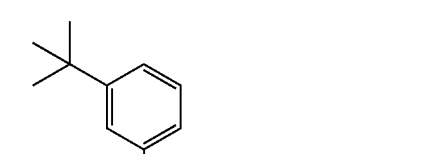 |
| 15 | 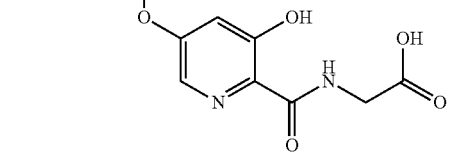 |
| 16 | 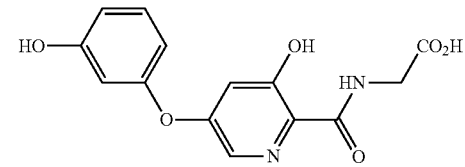 [SMILES: O=C(O)CNC(=O)c1ncc(Oc2cccc(O)c2)cc1O] |
|  | 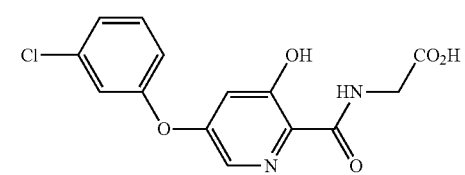 [SMILES: O=C(O)CNC(=O)c1ncc(Oc2cccc(Cl)c2)cc1O] |

-continued
| Compound | Structure |
|---|---|
| 17 | 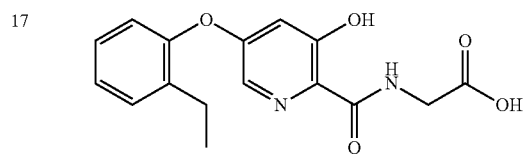 |
| 18 | 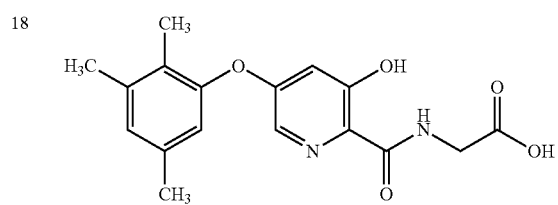 |
| 19 | 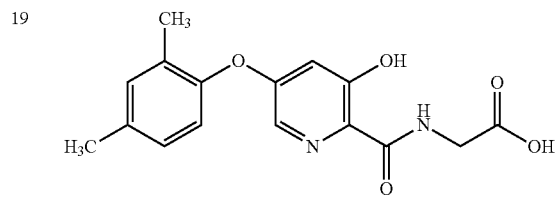 |
| 20 | 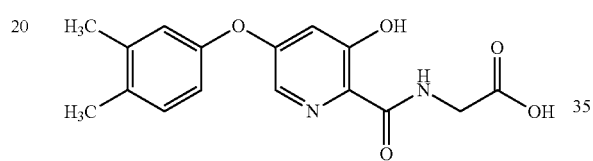 |
| 21 | 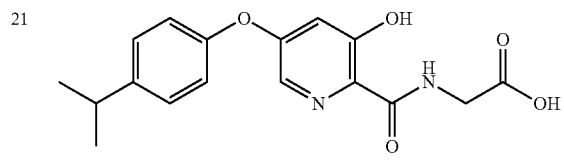 |
| 22 | 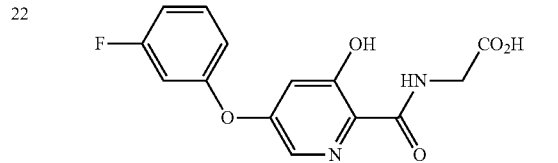 |
| 23 | 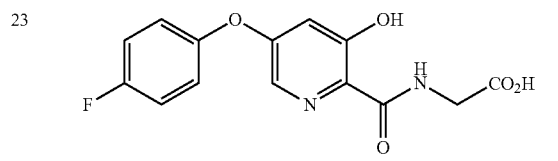 |
| 24 | 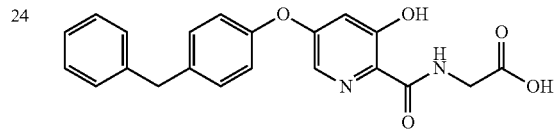 |
-continued
| Compound | Structure |
|---|---|
| 25 | 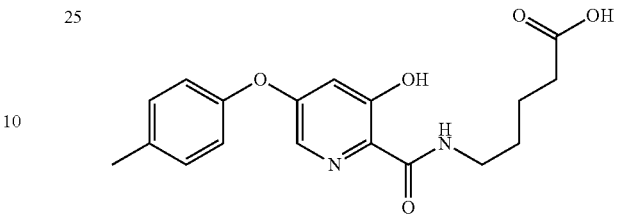 |
| 26 | 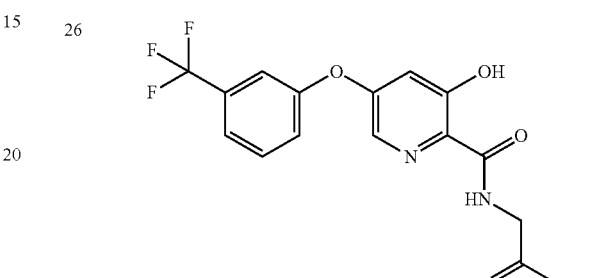 |
| 27 | 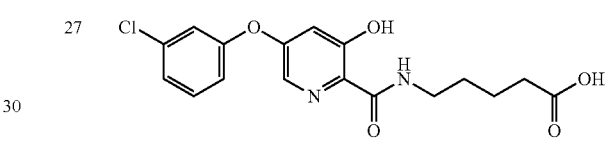 |
| 28 | 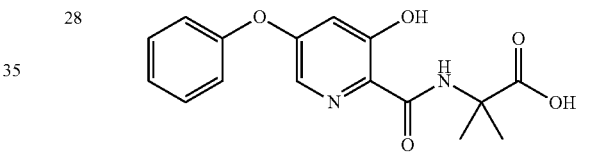 |
| 29 | 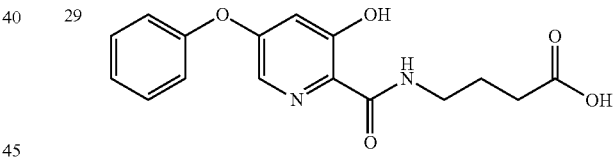 |
| 30 | 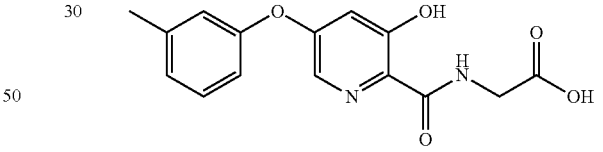 |
| 31 | 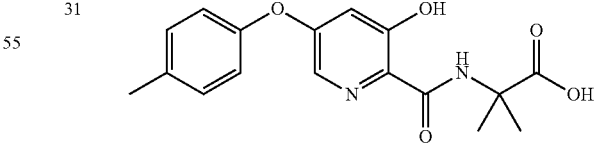 |
| 32 | 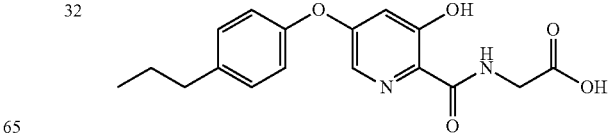 |

| Compound | Structure |
|---|---|
| 33 | 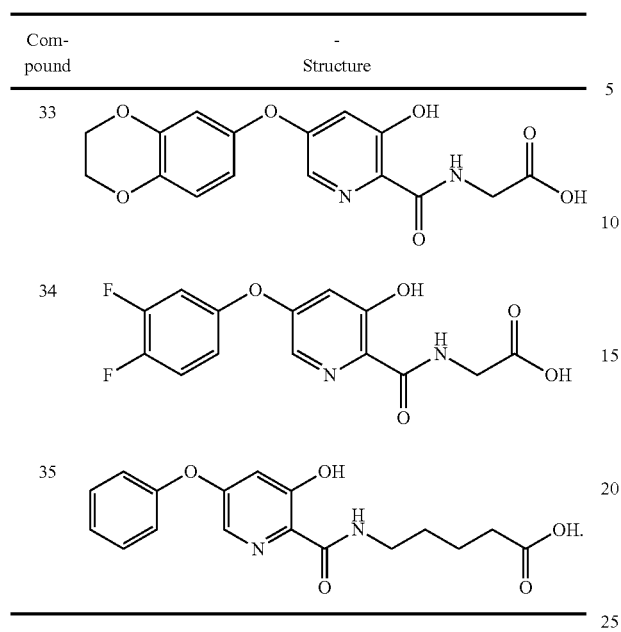 |
| 34 | 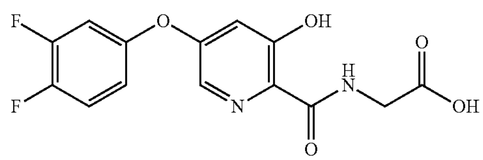 [SMILES: O=C(O)CNC(=O)c1ncc(Oc2ccc(F)c(F)c2)cc1O] |
| 35 | 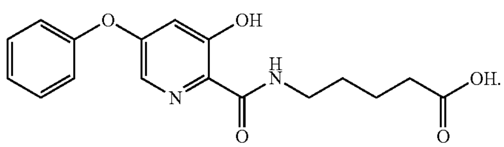 [SMILES: O=C(O)CCCCNC(=O)c1ncc(Oc2ccccc2)cc1O] |

5. A method for preparing the compound of claim 1, comprising the following steps:

step 1: reacting 5-bromo-3-fluoropyridyl-2-carbonitrile

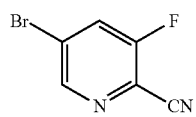

with sodium methoxide in the presence of methanol, to form 5-bromo-3-methoxypyridine-2-carbonitrile (intermediate III)

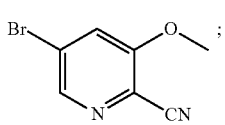

step 2: mixing and heating the intermediate (III) obtained in the step 1 with ArOH and a ligand in a solvent, and subjecting to an Ullman reaction in the participation of a catalyst to form an ether intermediate (IV)

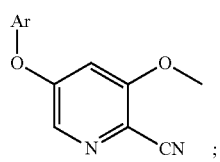

step 3: subjecting the intermediate (IV) obtained in the step 2 and hydrobromic acid/glacial acetic acid to hydrolysis reaction under reflux, to form a 3-hydroxypyridine-2-methanoic acid derivative (V)

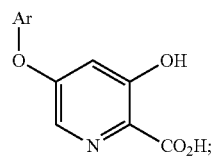

step 4: subjecting the intermediate (V) obtained in the step 3 and α-$R_3$-substituted amino acid benzyl ester (VI) to an amidation reaction in the presence of a condensing agent, to form a benzyl 3-hydroxypyridine-2-carboxylate intermediate (VII);

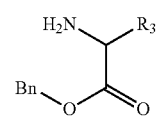

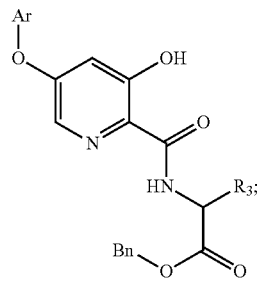

step 5: subjecting the intermediate (VII) obtained in the step 4 to hydrogenolysis reaction under hydrogenolysis conditions in a solvent in the presence of a catalyst at room temperature to remove the benzyl protecting group, to finally form a compound corresponding to Formula I or II;

wherein Ar represents

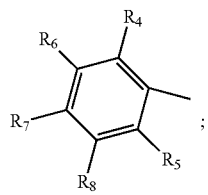

wherein $R_1$, $R_3$, $R_4$-$R_8$ are as defined in claim 1.

6. The method of claim 5, wherein the catalyst in the step 2 is cuprous$^{(I)}$ iodide; the metal ligand is selected from the group consisting of N, N-dimethylglycine, N-methylproline, N, N-tetramethylethylenediamine; the reaction solvent is selected from the group consisting of 1,4-dioxane, toluene, tetrahydrofuran; the step comprises carrying out the reaction by heating to 70° C. to 120° C.; in the step 3, the ratio of hydrobromic acid to glacial acetic acid is 2:1~1:3, the reaction temperature is 90~140° C., the heating reaction time is 6~12 hours; in the step 4, the α-$R_3$ amino acid benzyl ester (VI) is a hydrochloride form selected from the group consisting of glycine benzyl ester hydrochloride, (α or β) alanine benzyl ester hydrochloride, (α or β) valine benzyl ester hydrochloride, (α or β) leucine benzyl ester hydrochloride, (α or β) isoleucine benzyl ester hydrochloride, the solvent is selected from the group consisting of dichloromethane, chloroform, tetrahydrofuran, 1,4-dioxane, N,N-dimethylformamide, N-methylpyrrolidone; the amidation catalyst is selected from the group consisting of 1-(3-dimethylaminopropyl)-3-ethylcarbodiimide hydrochloride, 1-hydroxybenzotriazole, dicyclohexylcarbodiimide; in the step 5, the catalyst is selected from the group consisting of palladium$^{(0)}$/carbon, palladium$^{(II)}$ hydroxide, palladium$^{(II)}$ hydroxide/carbon, platinum dioxide, the solvent for hydrogenolysis is selected from the group consisting of methanol, ethanol, isopropanol, tetrahydrofuran, ethyl acetate.

7. A pharmaceutical composition, comprising a compound of claim 1 or a pharmaceutically acceptable salt thereof, and a pharmaceutically acceptable carrier.

8. A method for inhibiting HIF prolyl hydroxylase in a subject, comprising administering to the subject a compound of claim 1 or a pharmaceutically acceptable salt thereof.

9. A method for promoting the generation of endogenous EPO in a subject, comprising administering to the subject a compound of claim 1 or a pharmaceutically acceptable salt thereof.

10. A method for stabilizing hypoxia-inducible factor α in a subject, comprising administering to the subject a compound of claim 1 or a pharmaceutically acceptable salt thereof.

11. A method for treating chronic disease-related anemia in a subject, comprising administering to the subject a compound of claim 1 or a pharmaceutically acceptable salt thereof.

12. The method of claim 11, wherein the chronic disease-related anemia is selected from the group consisting of rheumatoid arthritis, rheumatism and inflammatory bowel disease.

13. A method for increasing the production of inflammatory cytokines in a subject, comprising administering to the subject a compound of claim 1 or a pharmaceutically acceptable salt thereof.

14. The method of claim 13, wherein the inflammatory cytokines include tumor necrosis factor, interleukin and interferon.

15. A method for treating anemia in a subject that is resistant to the treatment of exogenous administration of erythropoietin, comprising administering to the subject a compound of claim 1 or a pharmaceutically acceptable salt thereof, wherein the compound enhances the response of hematopoietic precursor cells to the erythropoietin.

16. A method for increasing the production of a factor required for iron ingestion, iron transport and iron utilization in a subject, comprising administering to the subject a compound of claim 1 or a pharmaceutically acceptable salt thereof, wherein the factor is selected from the group consisting of erythrocyte aminolevulinic acid synthase, transferrin, transferrin receptor and plasma ceruloplasmin.

* * * * *